(12) United States Patent
Lalonde

(10) Patent No.: US 8,747,352 B1
(45) Date of Patent: Jun. 10, 2014

(54) BALLOON DEFLECTION

(71) Applicant: Medtronic CyroCath LP, Toronto (CA)

(72) Inventor: Jean-Pierre Lalonde, Candiac (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 0 days.

(21) Appl. No.: 13/747,769

(22) Filed: Jan. 23, 2013

(51) Int. Cl.
*A61M 31/00* (2006.01)
*A61M 37/00* (2006.01)

(52) U.S. Cl.
USPC ............... 604/95.04; 604/96.01; 604/103.13; 606/194

(58) Field of Classification Search
USPC .......... 604/95.01, 95.04, 96.01, 528, 103.13; 600/585; 606/194
See application file for complete search history.

(56) References Cited

U.S. PATENT DOCUMENTS

| | | | |
|---|---|---|---|
| 4,723,936 A * | 2/1988 | Buchbinder et al. ....... | 604/95.01 |
| 4,998,917 A | 3/1991 | Gaiser et al. | |
| 5,030,204 A | 7/1991 | Badger et al. | |
| 5,254,088 A | 10/1993 | Lundquist et al. | |
| 5,397,305 A | 3/1995 | Kawula et al. | |
| 5,474,537 A | 12/1995 | Solar | |
| 7,137,990 B2 * | 11/2006 | Hebert et al. ................ | 606/194 |
| 7,273,468 B2 | 9/2007 | Bedell | |
| 7,351,214 B2 | 4/2008 | Burgermeister | |
| 7,381,198 B2 | 6/2008 | Noriega et al. | |
| 7,591,813 B2 | 9/2009 | Levine et al. | |
| 7,955,298 B2 | 6/2011 | Carroll et al. | |
| 2005/0075661 A1 | 4/2005 | Levine et al. | |
| 2006/0271090 A1 | 11/2006 | Shaked et al. | |
| 2011/0190831 A1 | 8/2011 | Mafi et al. | |

FOREIGN PATENT DOCUMENTS

| | | |
|---|---|---|
| EP | 0621794 B1 | 5/1997 |
| EP | 1179995 B1 | 1/2007 |
| WO | 2011153434 A2 | 12/2011 |

OTHER PUBLICATIONS

International Search Report and Written Opinion dated Feb. 27, 2014 for International Application Serial No:PCT/CA2013/001054, International Filing Date: Dec. 17, 2013 consisting of 9 pages.

* cited by examiner

*Primary Examiner* — Theodore Stigell
(74) *Attorney, Agent, or Firm* — Christopher & Weisberg, P.A.

(57) ABSTRACT

A medical device having enhanced steerability for navigation through a patient's vasculature and for positioning the device for performing a medical procedure, such as pulmonary vein isolation. The device generally includes an elongate body, a balloon defining a proximal neck that is affixed to the distal end of the elongate body such that the neck and elongate body are coterminous, a shaft disposed at least partially within the elongate body and at least partially within the balloon, and a pull wire affixed to a distal portion of the shaft, such that pulling the pull wire will cause deflection of the balloon at a point that is immediately distal of the proximal neck of the balloon. Further, the shape of the balloon when deflected and when in a neutral configuration may be substantially the same.

18 Claims, 6 Drawing Sheets

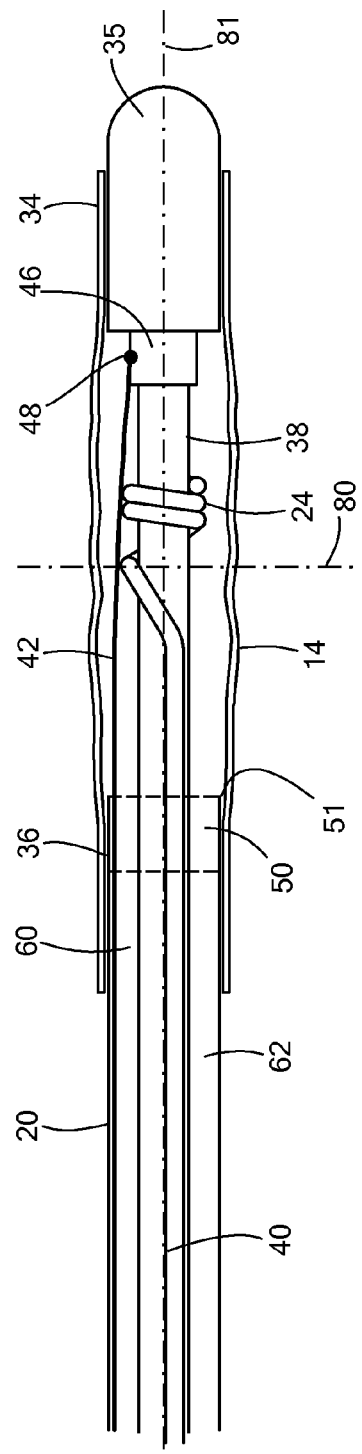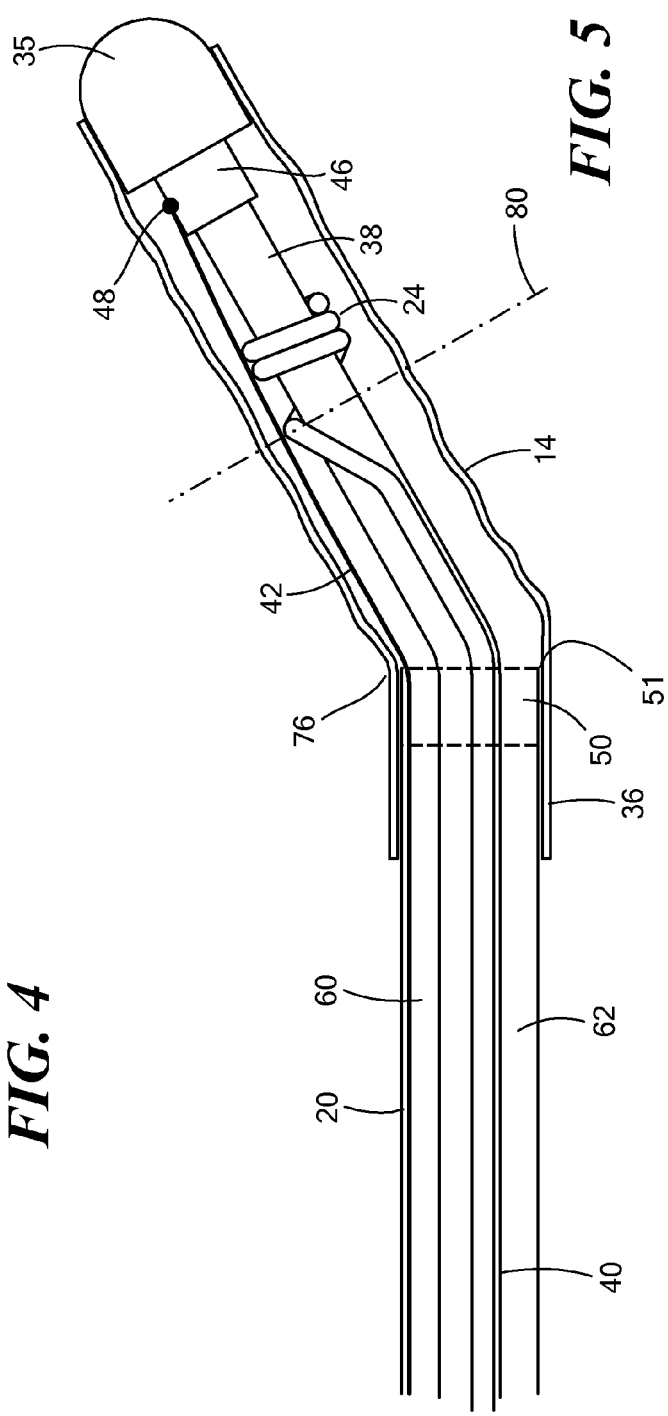

BALLOON DEFLECTION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for enhancing catheter steerability to facilitate catheter positioning before and during cardiac medical procedures. In particular, the present invention relates to a balloon catheter having increased deflection of the balloon.

BACKGROUND OF THE INVENTION

Cardiac arrhythmia is a condition in which the heart's normal rhythm is disrupted. There are many types of cardiac arrhythmias, including supraventricular arrhythmias that begin above the ventricles (such as premature atrial contractions (PACs), paroxysmal supraventricular tachycardia (PSVT), accessory pathway tachycardias, atrial fibrillation, and AV nodal reentrant tachycardia (AVNRT), ventricular arrhythmias that begin in the lower chambers of the heart (such as premature ventricular contractions (PVCs), ventricular tachycardia (VT), ventricular fibrillation, and long QT syndrome), and bradyarrhythmias that involve slow heart rhythms and may arise from disease in the heart's conduction system.

Atrial fibrillation (AF) is the most common cardiac arrhythmia, in which disorganized electrical impulses (usually generated by the roots of the pulmonary veins) interrupt the normal electrical impulses generated by the sinoatrial node, which in turn causes an irregular conduction of electrical impulses to the heartbeat-generating ventricles. AF may result from a number of conditions, such as hypertension, coronary artery disease, pericarditis, lunch disease, hyperthyroidism, carbon monoxide poisoning, or rheumatoid arthritis. Indeed, AF itself may increase the likelihood of stroke by as much as sevenfold.

Catheter ablation is frequently used to treat AF, and involves a minimally invasive procedure by which areas of cardiac tissue that facilitate the irregular electrical conduction are ablated using any of a number of energy modalities. For example, one or more pulmonary veins (PVs) may be targeted. AF is commonly initiated by foci located in the PVs, which are large blood vessels that carry oxygenated blood from the lungs to the left atrium (LA) of the heart. In order to disrupt the propagation of abnormal electrical currents, the ablation catheter may be placed around the opening of the PV to the heart and/or within the PV where the foci are located. However, the PVs are usually not regularly shaped, and often have an asymmetrical interior that can be difficult to navigate. Further, it can be very difficult to navigate a catheter through the septum and into the PVs, particularly the right inferior PV. Balloon catheters may be used to ablate within or on the ostium of a PV, but it is often difficult to properly seat the balloon within the vein or at the ostium to ensure proper tissue contact and/or occlusion of the vein.

Accordingly, it is desired to provide a catheter that is more easily navigated within a patient's vasculature and can be more accurately positioned for performing certain medical procedures, such as pulmonary vein isolation in the treatment of cardiac arrhythmia, such as atrial fibrillation, while reducing the risk of patient injury.

SUMMARY OF THE INVENTION

The present invention advantageously provides a device and system for improved catheter deflection and steerability. In one embodiment, the device may generally include an expandable element defining a proximal portion, a distal portion, and a lumen, an elongate body defining a proximal portion, a distal portion, and a lumen therebetween, the expandable element being affixed to at least a portion of the distal portion of the elongate body, a shaft disposed at least partially within the lumen of the expandable element and defining a proximal portion, a distal portion, and a longitudinal axis, and a pull wire attached to the distal portion of the shaft at an attachment point that is within the distal portion of the expandable element. The expandable element may be a balloon that defines a proximal neck and a distal neck, and the proximal neck may be affixed to at least a portion of the distal portion of the elongate body. Further, the proximal neck and the distal portion may be coterminous. When a pull force is exerted on the pull wire, the balloon may be deflected at an area that is proximal of the balloon lumen and immediately distal of the proximal neck of the balloon. Additionally, the balloon shape when deflected and when in a neutral position may be the same. The balloon may further define a midpoint that lies in a plane that is substantially orthogonal to the longitudinal axis of the shaft, and the plane may substantially bisect the balloon. Further, the pull wire attachment point may be on a distal portion of the shaft that is distal of the midpoint of the balloon.

In another embodiment, the device may generally include an elongate body defining a proximal portion, a distal portion, a lumen therebetween, and a longitudinal axis, a balloon defining a shape, a proximal portion, a distal portion, a lumen, and a midpoint, the proximal portion being affixed to the distal portion of the elongate body, a shaft disposed at least partially within the lumen of the balloon and at least partially within the lumen of the elongate body, and defining a proximal portion, a distal portion, and a longitudinal axis, the midpoint of the balloon lying in a plane that is substantially orthogonal to the longitudinal axis of the shaft, and the balloon proximal portion being proximal of the midpoint and the balloon distal portion being distal of the midpoint, and a pull wire attached to the distal portion of the shaft at an attachment point that is within the distal portion of the balloon, a pull force exerted on the pull wire deflecting the balloon in a deflection area that is proximal of the balloon lumen, the shape of the balloon when deflected and when the longitudinal axes of the shaft and elongate body are substantially coaxial being substantially the same.

In another embodiment, the device may generally include an elongate body defining a proximal portion, a distal portion, and a lumen therebetween, a balloon defining a shape, a proximal neck, a distal neck, a lumen, and a midpoint, the proximal neck being affixed to and coterminous with the distal portion of the elongate body, a shaft disposed at least partially within the lumen of the balloon and at least partially within the lumen of the elongate body, and defining a proximal portion, a distal portion, and a longitudinal axis, the midpoint of the balloon lying in a plane that is substantially orthogonal to the longitudinal axis of the shaft, and a pull wire attached to the distal portion of the shaft at an attachment point that is within the balloon lumen distal of the midpoint, a pull force exerted on the pull wire deflecting the balloon in a deflection area that is immediately distal of the balloon proximal neck, the shape of the balloon when deflected and when in a neutral position being substantially the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 4 shows a balloon catheter in a neutral position having enhanced steerability, the balloon being deflated for delivery to a target treatment site; and FIG. 5 shows a balloon catheter in a deflected position, the balloon being deflated for delivery to a target treatment site.

DETAILED DESCRIPTION OF THE INVENTION

As used herein, the term "enhanced steerability" or "enhanced deflection" may refer to a device's ability to be effectively deflected in one or more directions during navigation through a patient's body, including introducing the device through the patient's vasculature and positioning the device proximate a target treatment site (for example, a pulmonary vein in the left atrium). The term may also refer to the device's ability to deflect at one or more predetermined deflection points, which may allow an expandable element such as a balloon to be precisely positioned within a patient's vasculature or relative to a target area of tissue during a medical procedure. For example, a device having enhanced steerability may be more accurately aligned within, and thus more effectively occlude, a hollow anatomical feature (for example, a pulmonary vein) during cryoablation. In contrast to presently known devices, the present invention provides a device in which deflection of an expandable element coupled to the distal portion of the elongate body occurs at a deflection point that is proximal of an expanded portion of the balloon (as shown and described in greater detail in FIG. 3).

As used herein, the term "distal portion of the elongate body" refers to a portion of the elongate body that includes the distal terminus of the elongate body. The distal portion may begin at a point that is at least halfway between the proximal terminus and distal terminus of the elongate body. The portion of the elongate body not included in the distal portion may be considered to be the proximal portion.

As used herein, the term "distal portion of the balloon" refers to a portion of the balloon that includes the balloon distal neck and at least a portion of the balloon and balloon lumen. In particular, the distal portion of the balloon includes approximately half of the balloon and balloon lumen. Likewise, the term "proximal portion of the balloon" refers to a portion of the balloon that includes the balloon proximal neck and at least a portion of the balloon and balloon lumen. In particular, the proximal portion of the balloon includes approximately half of the balloon and balloon lumen.

Figure 1:
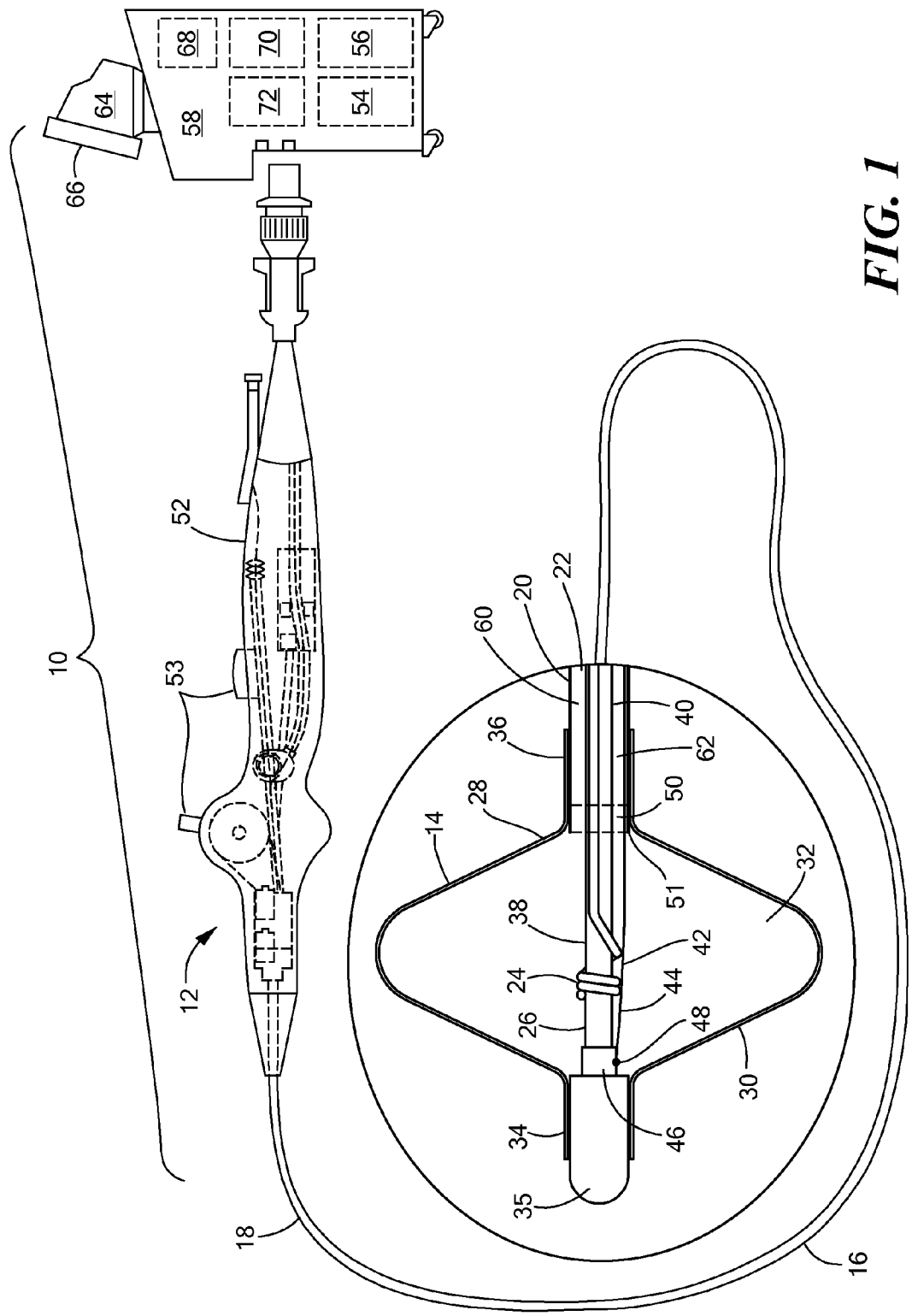
FIG. 1 shows a system that includes a balloon catheter having enhanced steerability.

Referring now to FIG. 1, a system 10 that includes a balloon catheter 12 having enhanced steerability is shown. The cryoablation system 10 may be used with a device such as a balloon catheter 12 having at least one balloon 14 or other expandable element. For example, a non-compliant balloon 14 may be used that is suitable for occluding a pulmonary vein or ostium of a pulmonary vein. Alternatively, the catheter 12 may include two balloons 14, 14c (as shown in FIG. 2C), and as a non-limiting example, the inner balloon 14 may be substantially non-compliant whereas the outer balloon 14c may be substantially compliant. The catheter 12 may include an elongate body 16 defining a proximal portion 18, a distal portion 20, and one or more lumens 22 therebetween, such as fluid, mechanical, or electrical lumens. The elongate body 16 may be passable through a patient's vasculature and/or proximate to a tissue region for diagnosis or treatment, such as a catheter, sheath, or intravascular introducer. The catheter 12 may further include a fluid injection element 24, and a flexible and resilient shaft 26 that is at least partially disposed within the elongate body 16. Further, the shaft 26 may be slidably and/or rotatably received within a lumen 22 of the elongate body 16, such that extension and retraction of the shaft 26 will alter the shape of the balloon 14. Alternatively, the shaft 26 may be affixed, and not slidable, within the elongate body 16. The balloon 14 may define a proximal portion 28, a distal portion 30, and a lumen 32 within which at least a part of the shaft 26 is disposed. Further, the distal portion 30 of the balloon 14 may include a neck region 34 that is affixed to a portion of the shaft 26, such as the shaft distal cap 35, as shown in FIGS. 1-3. Likewise, the proximal portion 28 of the balloon 14 may include a neck region 36 that is affixed to a portion of the elongate body 16, such as to an external surface of the elongate body 16, as shown in FIGS. 1-3.

Figure 2A:
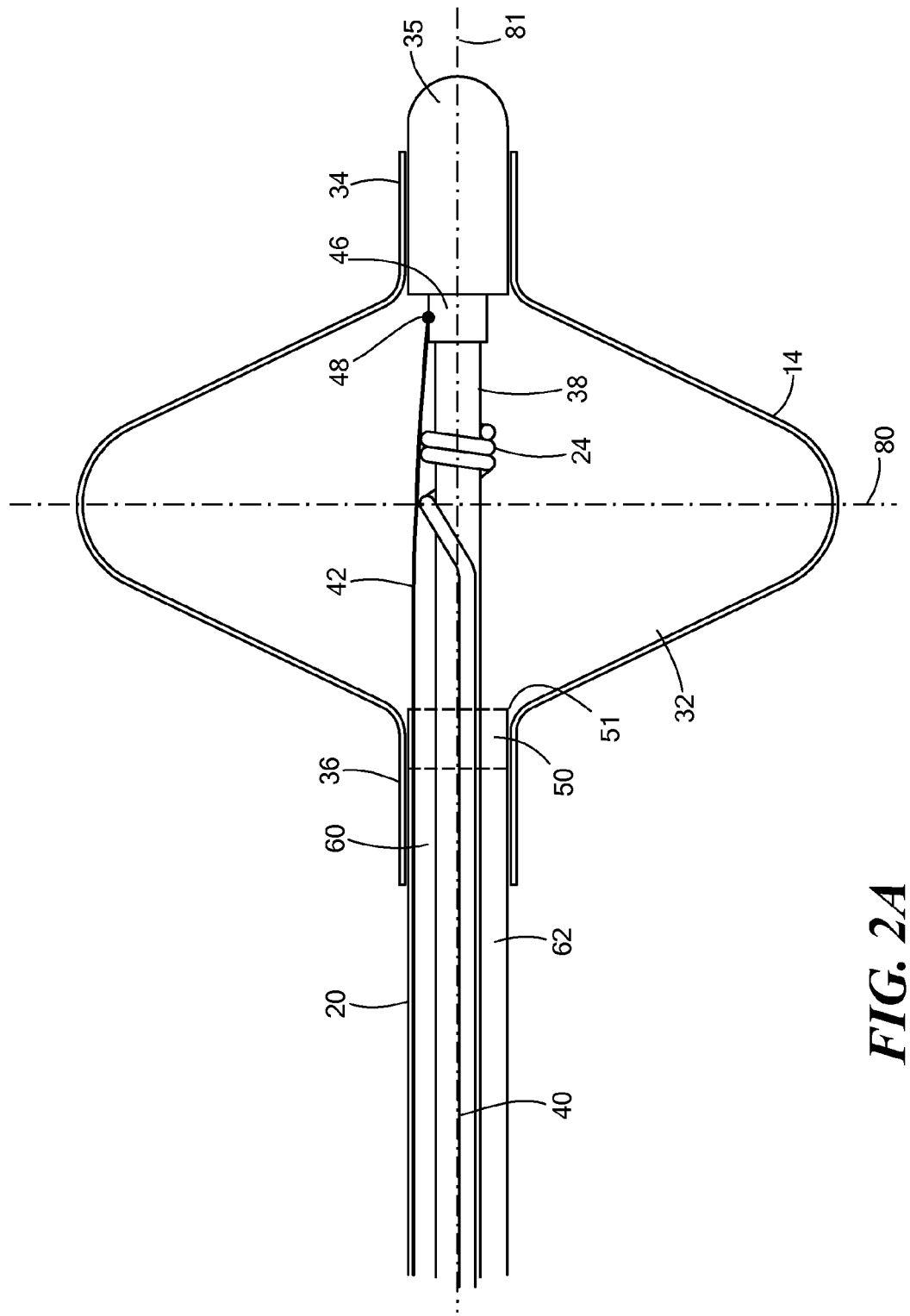
FIG. 2A shows a first embodiment of a balloon catheter in a neutral position having enhanced steerability, the device including a pull wire that is coupled to the shaft within a distal portion of the balloon.
Figure 2B:
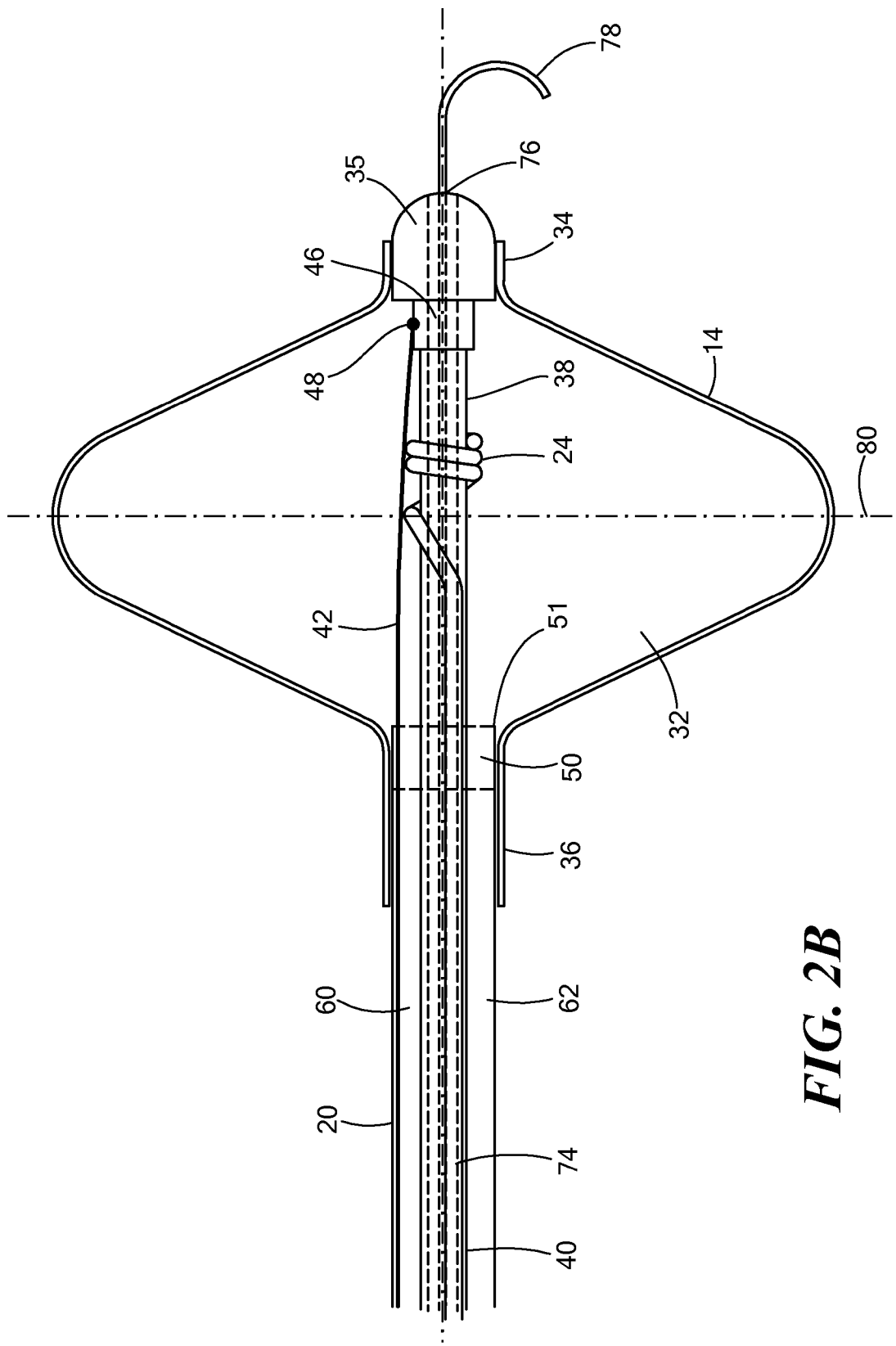
FIG. 2B shows a second embodiment of a balloon catheter in a neutral position having enhanced steerability, the device including a pull wire that is coupled to the shaft within a distal portion of the balloon.
Figure 2C:
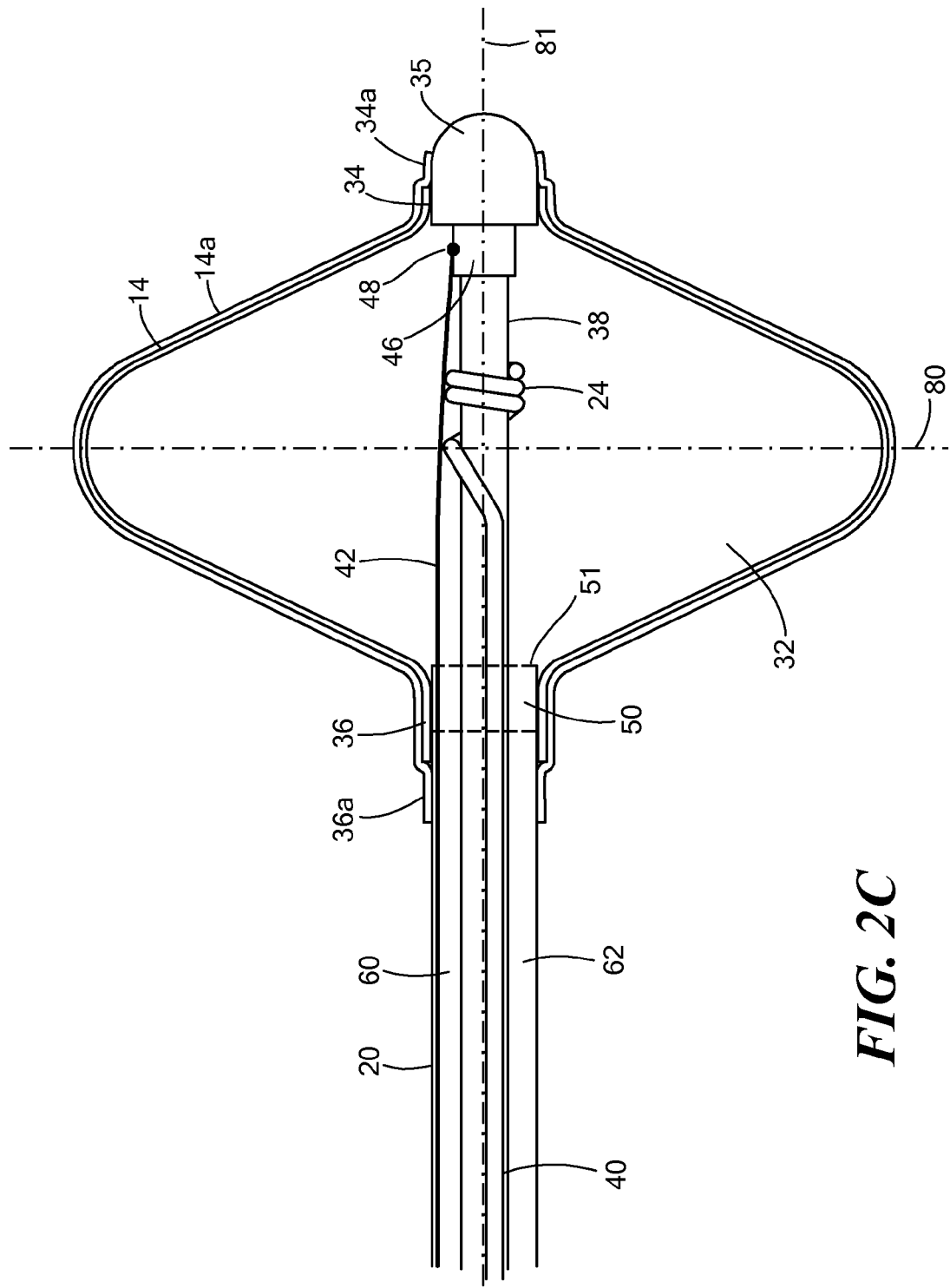
FIG. 2C shows a third embodiment of a balloon catheter in a neutral position having enhanced steerability, the device including a pull wire that is coupled to the shaft within a distal portion of the balloon.
Figure 3:
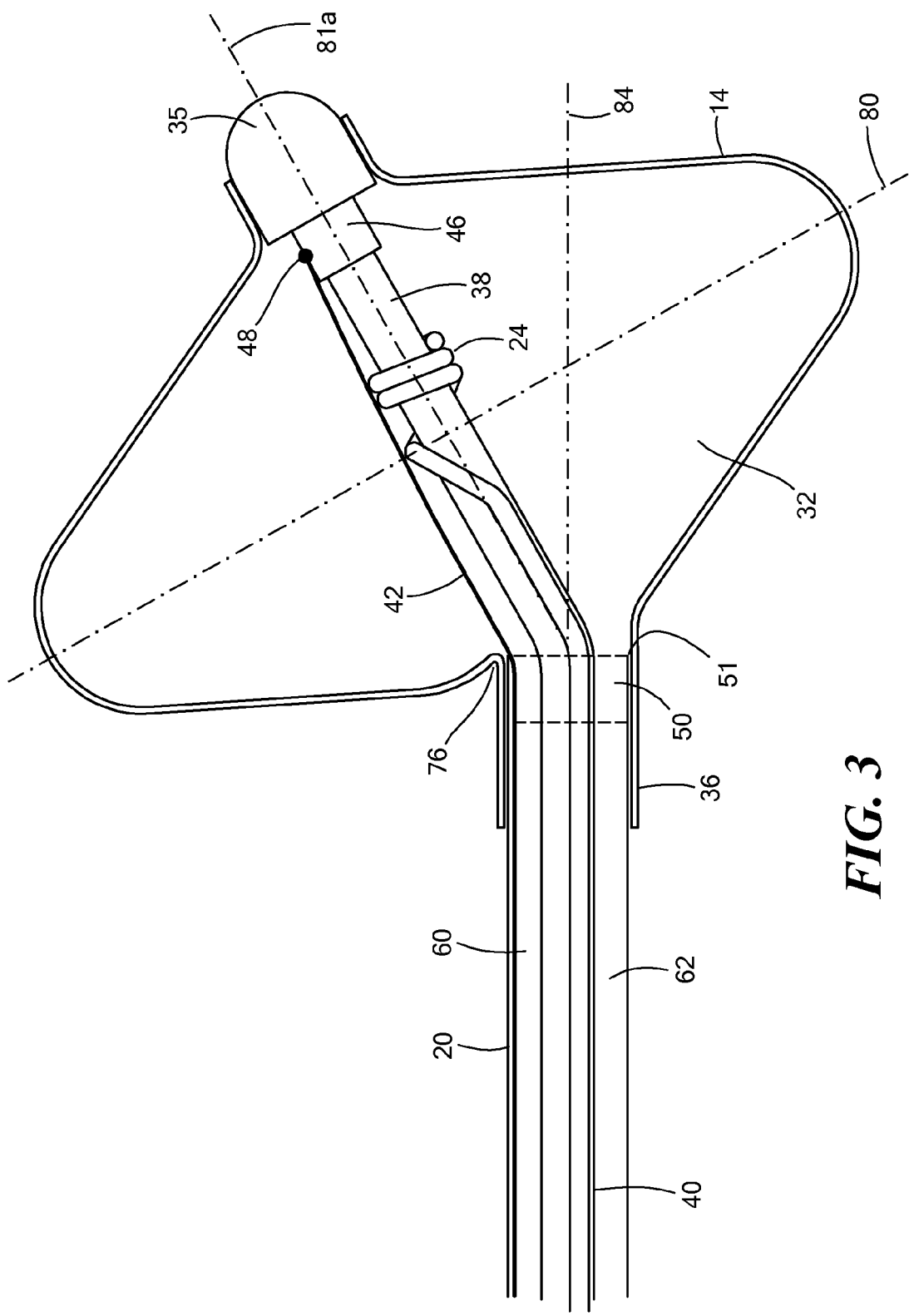
FIG. 3 shows a balloon catheter in a deflected position, the deflection point being located proximal of the balloon lumen.

As is further shown in FIGS. 1-3, the shaft 26 may pass through the entirety of the balloon lumen 32, exiting or extending beyond the distal portion 20 of the elongate body 18 and being at least coterminous with the distal portion 30 of the balloon 14. However, the shaft 26 may extend beyond the distal portion 30 of the balloon 14, as described in more detail in FIGS. 2A-2C. The portion of the shaft 26 that extends beyond the elongate body 18 may be referred to as the shaft distal portion 38, whereas the portion of the shaft 26 that is disposed within the elongate body may be referred to as the shaft proximal portion 40.

The catheter 12 may further include a pull wire 42 that is operationally coupled to the shaft 26 at a location that is eccentric to the shaft 26. That is, the pull wire 42 is coupled to one side of the shaft 26 in an off-center location, and pulling the pull wire 42 will deflect the shaft 26 in the direction in which the pull force is exerted. The more the shaft 26 deflected, the less pull force is required to deflect the shaft 26 further. Although a single pull wire 42 is shown in FIGS. 1-3, any number of pull wires 42 may be included. The pull wire 42 may define a distal portion 44 and a proximal portion (not shown), with the distal portion 44 being affixed or coupled to the distal portion 38 of the shaft 26. For example, the pull wire distal portion 44 may be coupled to a ring, sleeve, sheath, or other coupling element 46 at an attachment point 48. The coupling element 46 may be affixed to and/or disposed about the distal portion 38 of the shaft 26. The coupling element may also be coupled to and/or located proximal to the shaft distal cap 35. For example, the coupling element 46 is shown in FIGS. 1-3 to be immediately proximal the shaft distal cap 35. Alternatively, the pull wire distal portion 44 may be coupled directly to the shaft 26 at an attachment point 48. The elongate body 16 may have a durometer that is greater than that of the shaft 26, so that the shaft 26 bends more readily than the elongate body 16 when a pull force is exerted on the pull wire 42. Further, the elongate body may include a protective element 50 at the distal end 51 of the elongate body 16 that protects the elongate body 16 and/or balloon 14 from perforation or abrasion by the pull wire 42 when a pull force is exerted on the pull wire 42 and the balloon 14 is deflected. The protective element 50 may also help strengthen or stiffen the distal end 51 of the elongate body 16 to encourage preferential bending at the deflection point, as described in more detail in FIG. 3. For example, the protection element 50 may be a metal sleeve, cuff, collar, or ring within the elongate body 16, at or proximate the distal end 51. Alternatively, the protection element 50 may be a tube or conduit within which the pull wire 42 is disposed, the tube or conduit being substantially coterminous with the distal end 51 of the elongate body. Such a tube or conduit may extend throughout the elongate body 16, all the way to the handle 52 of the device 12, or it may extend throughout only a portion of the elongate body 16 from the distal end 51.

The catheter 12 may include a handle 52 coupled to the proximal portion 18 of the elongate body 16. The handle 52 may include one or more actuators, wheels, knobs, or other steering control elements 53 in communication with the pull wire 42 and/or shaft 26. For example, the proximal portion of the pull wire 42 may be operably coupled to a steering control elements 53 such that manipulation of the steering control element 53 may exert or release a pulling force on the pull wire 42 that deflects the shaft 26 and, as a result, the balloon 14. Further, the handle 52 may include circuitry for identification and/or use in controlling of the medical device 12 or another component of the system 10. For example, the handle 52 may include one or more pressure sensors to monitor the fluid pressure within the catheter 12. The handle 52 may also include connectors that are matable directly to a fluid reservoir 54, fluid recovery reservoir 56, and console 58 or indirectly by way of one or more umbilicals. The handle 52 may further include blood detection circuitry in fluid and/or optical communication with a fluid delivery lumen 60 and fluid recovery lumen 62. The handle 52 may also include a pressure relief valve in fluid communication with the fluid delivery conduit 60 and/or fluid recovery conduit 62 to automatically open under a predetermined threshold value in the event that value is exceeded.

The system 10 may also generally include a control unit or operating console 58 in communication with the catheter 12. The console 58 may include one or more computers 64, each having a display 66, one or more user input devices, and one or more processors for executing algorithms, programs, and/or calculations, and for generating images, alerts, maps, instructions, system feedback or status signals, and/or user input options on the display 66. The system 58 may further include one or more coolant reservoirs 54, coolant recovery reservoirs 56, power sources 68, energy generators 70, and/or vacuum pumps 72 for evacuating expanded coolant from the balloon lumen 32. The medical device 12 may generally include one or more treatment regions, for example, one or more cryoballoons 16, for energetic or other therapeutic interaction between the medical device 12 and a treatment site. Although the system 10 described herein is used at least for cryogenic treatments, the system 10 may also be configured to deliver, for example, radiofrequency energy, microwave energy, ultrasound energy, or provide other energetic transfer with a tissue area in proximity to the treatment regions, including cardiac tissue.

Referring now to FIGS. 2A and 2B, a first and second embodiment of a balloon catheter 12 in a neutral position having enhanced steerability is shown, the catheter 12 including a pull wire 42 that is coupled to the shaft 26 within a distal portion of the balloon 14. The catheter 12 is generally as shown and described in FIG. 1. However, the embodiment of FIG. 2A includes a shaft distal cap 35 that shorter than the shaft distal cap 35 of the embodiment in FIG. 2B. Although a shorter distal cap 35 may be more easily navigated through a patient's vasculature, the shorter distal cap 35 may provide a reduced area to which the distal neck 34 of the balloon may be affixed. Conversely, although the longer distal cap 35 may provide a larger area to which the distal neck 34 of the balloon 14 may be affixed, the longer distal cap 35 may make navigation somewhat more difficult. Thus, the distal cap 35 may be selected according to the requirements of the procedure in which the catheter 12 will be used. Further, as shown in the embodiment of FIG. 2B, the shaft 26 may define a lumen 74 and an opening 76 through which a guide wire 78 may be passed to help locate, for example, the pulmonary veins, prior to inflation of the balloon 14. The enhanced deflection of the catheter 12 may greatly facilitate rapid and accurate location of the pulmonary veins because the catheter 12 may be deflected before the balloon 14 is inflated to direct the guide wire 78 toward a target pulmonary vein. In currently known devices with a more limited distal deflection range, finding a pulmonary vein with the guide wire is very difficult and involves an amount of trial and error. Once a pulmonary vein is located, the guide wire 78 may be advanced into the pulmonary vein. As a non-limiting example, the guide wire 78 may be expanded into a circular structure that is in contact with the inner wall of the pulmonary vein, thereby anchoring the guide wire 78. Once the guide wire 78 is in place, the balloon 14 may be inflated and advanced over the guide wire 78 until the balloon 14 is in contact with the ostium of the pulmonary vein. Not only does the enhanced steerability of the catheter 12 facilitate rapid and accurate location of a pulmonary vein with the guide wire 78 before the balloon 14 is inflated, but also helps to properly seat the inflated balloon 14 against a pulmonary vein ostium to ensure adequate occlusion of the ostium and good tissue contact for creating a substantially circumferential and transmural lesion. Both embodiments, however, include a pull wire 42 coupled to a distal portion 38 of the shaft 26. In particular, the location of the attachment point 48 may be proximate the distal neck 34 of the balloon 14, distal to the midpoint 80 of the balloon 14. Although referred to as a "midpoint," the midpoint 80 may be a plane (as shown in FIGS. 2A-3) that is substantially orthogonal to the longitudinal axis 81 of the shaft 26 and that substantially bisects the balloon into two approximately equal portions: the proximal portion 28 and the distal portion 30.

Referring now to FIG. 2C, a third embodiment of a balloon catheter 12 in a neutral position having enhanced steerability is shown, the catheter 12 including a pull wire 42 that is coupled to the shaft 26 within a distal portion of the balloon 14. The embodiment of FIG. 2C is similar to the embodiments of FIGS. 2A and 2B, except that the embodiment of FIG. 2C includes two balloons, an inner balloon 14 and an outer balloon 14c. Both balloons 14, 14c may be either substantially compliant or substantially non-compliant, or one balloon may be substantially compliant whereas the other balloon may be substantially non-compliant. As a non-limiting example, the inner balloon 14 may be substantially noncompliant, whereas the outer balloon 14c may be substantially compliant.

In FIGS. 2A-2C, the proximal neck region 36 of the balloon 14 (or at least the inner balloon 14, in the embodiment of FIG. 2C) may be affixed to the elongate body 16 all the way up to the distal end 51 of the elongate body 16. That is, the proximal neck region 36 and the distal portion 20 of the elongate body 16 may be coterminous at the distal end 51 of the elongate body 16.

Referring now to FIG. 3, a balloon catheter 12 in a deflected position is shown, the deflection point 82 being located proximal of the balloon lumen 32. As shown and described in FIGS. 1-2B, the location of the attachment point 48 between the pull wire 42 and shaft 26 may be proximate the distal neck 34 of the balloon 14, distal to the midpoint 80 of the balloon 14. This distally positioned attachment point 48 makes it possible to deflect the shaft 26 and, as a result, the balloon 14 (that is, portions of the device that are distal of the elongate end 51 of the elongate body 16), at a deflection point 82 that is proximal of the balloon lumen 32. The effect of the distally positioned attachment point 48 that is eccentric relative to the longitudinal axis 81 of the shaft 26 may be enhanced by the fact that the elongate body 16 may be more resistive to deflection than the shaft 26 and that the balloon proximal neck 36 is coupled to the elongate body 16 up to the distal end 51 of the elongate body 16. Therefore, the entirety of the balloon 14, excluding the proximal neck region 36, may be deflected to enhance steerability and/or to accurately position the balloon 14 to perform a medical procedure. The catheter 12 may be deflected without altering the size and/or shape of the balloon 14 itself. That is, the balloon size and shape when the balloon 14 is deflected (as shown in FIG. 3) may be substantially the same as the balloon size and shape when the balloon 14 is in a neutral position (as shown in FIGS. 1-2C). This may be important during pulmonary vein occlusion procedures, because proper alignment of the balloon 14 during a procedure within a pulmonary vein or at the ostium of a pulmonary vein, for example, may depend on maintaining the size and shape of the balloon 14 (particularly the diameter). Without good tissue contact effected by proper alignment of the balloon and prevention of changes in the balloon size and shape, it may not be possible to create permanent lesions in the tissue, for example, substantially circumferential and transmural lesions. Some procedures, such as cryoablation used to treat atrial fibrillation, are not effective unless permanent lesions are created. Further, the catheter 12 described herein has an angle of deflection that is greater than currently know devices, which greatly facilitates navigation into difficult areas, such as the right inferior PV. For example, once the device 12 is passed through the septum, the balloon 14 may be deflected to make a sharp turn required to not only accurately navigate the balloon 14 to the right inferior PV, but also to properly align the balloon 14 within the PV or PV ostium without having to force the balloon 14 against tissue to create a suitable balloon 14 orientation, which reduces the chance of perforating the tissue. However, it will be understood that the catheter 12 described herein may be used for any medical procedure, including cryotreatment (such as cryoablation or tissue cooling) of other hollow anatomical features or cryotreatment of substantially flat tissue, such as a cardiac wall.

As shown in FIG. 3, the deflection point 82 may be immediately distal of the proximal neck region 36 of the balloon 14 and immediately proximal of the balloon lumen 32. As discussed above, the distally positioned attachment point 48 makes it possible to deflect the shaft 26 and, as a result, the balloon 14, at a deflection point 82 that is proximal of the balloon lumen 32. The effect of the distally positioned attachment point 48 may be enhanced by the fact that the elongate body 16 may be more resistive to deflection than the shaft 26 and that the balloon proximal neck 36 is coupled to the elongate body 16 up to the distal end 51 of the elongate body 16. Therefore, the entirety of the balloon 14, excluding the proximal neck region 36, may be deflected to enhance steerability and/or to accurately position the balloon 14 to perform a medical procedure. Further, the balloon 14 may be deflected freely without altering the size or shape of the balloon 14. Although referred to as a "point," the deflection point 82 may be an imaginary ring that extends about the circumference of the balloon, so that a deflection point 82 may occur no matter in which direction the balloon 14 is deflected. When the catheter 12 is in a neutral position, the longitudinal axis of the shaft 81 and the longitudinal axial 84 of the elongate body 16 may be substantially coaxial. When the device 12 is in a deflected position (as shown in FIGS. 3 and 5), the shaft 26 is bent, so that the longitudinal axis 81a of the distal portion 38 of the shaft 26 is offset from the elongate body longitudinal axis 84.

Referring now to FIGS. 4 and 5, a balloon catheter 12 being in a neutral position and a deflected position is shown, respectively. The device 12 of FIGS. 4 and 5 may generally the same as any devices shown and described in FIGS. 1-3; however, the balloon 14 is shown in a deflated state in FIGS. 4 and 5, such as when the catheter 12 is being navigated through the patient's vasculature for delivery at a target treatment site. Even though the balloon 14 is not inflated, the balloon 14 (the area distal of the distal end 51 of the elongate body 16) may still be deflected at the deflection point 82 as described above.

The distally attached pull wire may also be used in other devices, such as focal catheters or catheters having a linear ablation area. In such an embodiment, the elongate body may include a lower durometer area that is more easily deflected than a higher durometer area proximal to the lower durometer area. Further, the pull wire may be coupled to an interior of the distal portion or to a shaft within the distal portion of the elongate body at a location that is distal to the lower durometer area, and the higher durometer area may include a protective element, so that exerting a pull force on the pull wire will preferentially deflect the elongate body at a deflection point that is at the junction of the higher durometer area and the lower durometer area.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
    an expandable element defining a proximal portion, a distal portion, and a lumen;
    an elongate body defining a proximal portion, a distal portion, and a lumen therebetween, the expandable element being affixed to at least a portion of the distal portion of the elongate body;
    a shaft disposed at least partially within the lumen of the expandable element and defining a proximal portion, a distal portion, and a longitudinal axis; and
    a pull wire having a continuous diameter, the pull wire being attached to the distal portion of the shaft at an attachment point that is within the distal portion of the expandable element, a pull force exerted on the pull wire deflecting the expandable element at a deflection point that is proximal of the balloon lumen.

2. The device of claim 1, wherein the expandable element is a balloon.

3. The device of claim 2, wherein the balloon further defines a proximal neck and a distal neck, the proximal neck being affixed to at least a portion of the distal portion of the elongate body.

4. The device of claim 3, wherein the proximal neck and the distal portion of the elongate body are coterminous.

5. The device of claim 4, wherein the deflection point is also immediately distal of the proximal neck of the balloon.

6. The device of claim 5, wherein the balloon shape when deflected and the balloon shape when in a neutral position are the same.

7. The device of claim 6, wherein the balloon is non-compliant.

8. The device of claim 6, wherein the balloon defines a midpoint that lies in a plane that is substantially orthogonal to the longitudinal axis of the shaft.

9. The device of claim 8, wherein the plane substantially bisects the balloon.

10. The device of claim 9, wherein the balloon proximal portion is proximal of the midpoint and the balloon distal portion is distal of the midpoint.

11. The device of claim 10, wherein the pull wire attachment point is on the distal portion of the shaft distal of the midpoint.

12. The device of claim 11, wherein the shaft includes a coupling element.

13. The device of claim 12, wherein the pull wire attachment point is on the coupling element.

14. The device of claim 4, wherein the shaft is at least partially disposed within the lumen of the elongate body.

15. The device of claim 14, wherein the distal neck is coupled to the distal portion of the shaft.

16. The device of claim 4, wherein the distal portion of the shaft defines a cap, the distal neck of the balloon being coupled to the cap.

17. The device of claim 4, further comprising a collar, wherein the distal portion of the elongate body defines a distal end, the collar being disposed within the elongate body at the distal end.

18. A medical device comprising:
an elongate body defining a proximal portion, a distal portion, a lumen therebetween, and a longitudinal axis;
a balloon defining a shape, a proximal portion, a distal portion, a lumen, and a midpoint, the proximal portion being affixed to the distal portion of the elongate body;
a shaft disposed at least partially within the lumen of the balloon and at least partially within the lumen of the elongate body, and defining a proximal portion, a distal portion, and a longitudinal axis, the midpoint of the balloon lying in a plane that is substantially orthogonal to the longitudinal axis of the shaft, and the balloon proximal portion being proximal of the midpoint and the balloon distal portion being distal of the midpoint; and
a pull wire having a continuous diameter, the pull wire being attached to the distal portion of the shaft at an attachment point that is within the distal portion of the balloon, a pull force exerted on the pull wire deflecting the balloon in a deflection area that is proximal of the balloon lumen, the shape of the balloon when deflected and when the longitudinal axes of the shaft and elongate body are substantially coaxial being substantially the same.

* * * * *